United States Patent [19]
Miller

[11] Patent Number: 5,880,469
[45] Date of Patent: Mar. 9, 1999

[54] METHOD AND APPARATUS FOR A DIRECTIONAL NEUTRON DETECTOR WHICH DISCRIMINATES NEUTRONS FROM GAMMA RAYS

[76] Inventor: Thomas Gill Miller, 254 Brentwood La., Madison, Ala. 35758

[21] Appl. No.: 803,893

[22] Filed: Feb. 21, 1997

Related U.S. Application Data

[63] Continuation-in-part of Ser. No. 380,953, Jan. 31, 1995, Pat. No. 5,606,167.

[51] Int. Cl.$^6$ ..................................................... G01N 1/20
[52] U.S. Cl. ................ 250/367; 250/370.06; 250/390.11
[58] Field of Search ............................. 250/367, 370.05, 250/370.06, 370.01, 390.01, 390.11, 390.12

[56] References Cited

U.S. PATENT DOCUMENTS

| | | |
|---|---|---|
| 4,380,817 | 4/1983 | Harding et al. . |
| 4,931,646 | 6/1990 | Koechner ................................ 250/367 |
| 5,155,366 | 10/1992 | Miller . |
| 5,200,626 | 4/1993 | Schultz et al. . |
| 5,278,418 | 1/1994 | Broadhurst . |
| 5,410,156 | 4/1995 | Miller . |

FOREIGN PATENT DOCUMENTS 3108687  5/1991  Japan .

OTHER PUBLICATIONS

"Guidelines for Preparing Responses to the Federal Aviation Administrations Broad Agency Announcement (BAA) for Aviation Security Research Proposals TCBAA 90–001", Federal Aviation Administration, Revision 3–Nov. 1, 1989.
"Determination of H, C. N, O Content of Bulk Materials from Neutron–Attenuation Measuremetn", J.C. Overley, Int. J. Radiat. Isot., vol. 36, No. 3, pp. 185–191, 1985.
"Explosive Detection System Based on Thermal Neutron Activation", IEEE AES Magazine, Dec. 1989.
"Nuclear–Based Techniques for Explosive Detection", T. Gozani, R. Morgado, C. Seher, Journal of Energetic Materials, vol. 4, pp. 377–414 (1986).
"PFNA Technique for the Detection of Explosives", Proc. Of First Int. Symp. On Explosives Det. Technology, FAA Tech Ctr., Atlantic City Int. Airport, NJ, Feb. 1992.

(List continued on next page.)

*Primary Examiner*—Edward P. Westin
*Assistant Examiner*—Richard Hanig
*Attorney, Agent, or Firm*—Baker & Botts, L.L.P.

[57] ABSTRACT

Apparatus and method for discriminating against neutrons coming from directions other than a preferred direction and discriminating against gamma rays. Two photomultiplier (PM) tubes 9,10 are parallel to each other and are attached to one end of a light pipe 12. A neutron scintillator 13 is attached to the other end of the light pipe. The scintillator 13 is comprised of optical fibers arranged contiguously along a first direction, which is perpendicular to a length dimension of the optical fibers, and which optical fibers alternate between optical fibers which emit photons only in the lower portion of the electromagnetic spectrum and optical fibers which emit photons only in the higher portion of the electromagnetic spectrum. Typically, the optical fibers are about 100–250 microns. Filters 7,8 are between the PM tubes and the light pipe. One filter 7 transmits only photons in the lower end of the electromagnetic spectrum and the other filter 8 transmits only photons in the higher portion of the electromagnetic spectrum. Neutrons proceeding from a source which is parallel to the first direction will tend to cause only one optical fiber to emit photons. If neutrons enter the scintillator perpendicular to such first direction, photons will most likely be emitted by more than one optical fiber. A signal processing unit 11 will register a detected neutron if a signal is received from only one PM tube and will register a background event if signals are received from both PM tubes. If a gamma ray enters the detector and is detected, the scattered Compton electron most likely will cross two or more optical fibers, causing signals in both PM tubes. A signal processing unit 11 will register the event as a background event.

33 Claims, 4 Drawing Sheets

OTHER PUBLICATIONS

"Fiber Optics Neutron Detectors", Thomas G. Miller, Welman Gebhart, Lee Hilbert and George Edlin, presented at the Workshop on Scintillating Fiber Detector Development for the SSC, Nov. 14–16, 1988.

"A Directional Neutron Counter for Neutrons", R.F. Stetson and S. Berko, Nuc. Instr. & Meth. 6 (1960) pp. 94–95.

"Directional Scintillation Counter", M.A. Thompson, Rev. Scien. Instr. 29 (1958), p. 1149.

METHOD AND APPARATUS FOR A DIRECTIONAL NEUTRON DETECTOR WHICH DISCRIMINATES NEUTRONS FROM GAMMA RAYS

CROSS-REFERENCE TO RELATED APPLICATION

This application is a continuation-in-part application to Ser. No. 08/380,953, filed on Jan. 31, 1995, now U.S. Pat. No. 5,606,167, in the name of Thomas G. Miller and entitled "contraband Detection Apparatus and Method," the subject matter of which is hereby incorporated by reference in its entirety. In addition, this application has similarities with Miller (U.S. Pat. No. 5,410,156) issued on Apr. 25, 1995 and Miller (U.S. Pat. No. 5,155,366) issued on Oct. 13, 1992.

This invention was made with government support under FAA Grant 94G-033 awarded by the Federal Aviation Administration. The government has certain rights in the invention.

FIELD OF THE INVENTION

This invention pertains to a method and apparatus for detecting neutrons from a neutron source in a field of background neutrons (neutrons coming from directions other than from the source) and gamma rays. In particular, the method and apparatus will discriminate against gamma rays and those neutrons coming from directions other than from the neutron source. This invention in general pertains to the detection of contraband and particularly to the detection and identification of explosives and illicit drugs concealed in luggage and the like.

PRIOR ART AND OTHER CONSIDERATIONS

Small amounts of modern explosives are easy to hide in airport luggage, cannot be detected by current systems, and can destroy an airplane. A workable system for detecting explosives in airport luggage is urgently needed. For practical use in an airport, each scan would have to be completed in seconds. A system this advanced does not exist and is not possible under current technology.

Current methods for detecting explosives in airport luggage use neutral particle probes, such as X-rays and neutrons, which can penetrate sealed luggage. However, existing systems cannot identify all of the elements which comprise explosives and have other shortcomings noted below.

X-ray systems are sensitive to differences in X-ray absorption coefficients in luggage. Because explosives have absorption coefficients similar to items commonly found in luggage, X-ray systems, including X-ray computed tomography (CT) scanners, have high false alarm rates.

Thermal neutron absorption (TNA) detects the n,γ reaction on nitrogen and so searches only for nitrogen. Since many non-explosive items found in luggage are rich in nitrogen, TNA has an unacceptably high false alarm rate. Other problems with TNA include that the neutrons must be thermalized, the n,γ cross section is in the millibarn range, it is difficult to obtain the spatial nitrogen concentration, and the background count rate is very high. "Explosive Detection System Based On Thermal Neutron Activation", IEEE AES Magazine, December 1989 and "Nuclear-Based Techniques for Explosive Detection", T. Gozani, R. Morgado, C. Seher, Journal of Energetic Materials, Vol. 4, pp. 377–414 (1986).

Pulsed fast neutron absorption (PFNA) detects the inelastic scattered gamma rays from nitrogen, carbon, and oxygen. Problems with PFNA include that the cross sections are in the millibarn range, background count rates are very high, determination of concentration as a function of position has large uncertainties, and it is difficult to make a gamma ray detector with adequate energy resolution and still maintain high count rate capability. "PFNA Technique for the Detection of Explosives", Proc. of First Int. Sym. on Explosives Det. Technology, FAA Tech. Ctr., Atlantic City Int. Airport, N.J., February 1992.

As noted above, existing nuclear-based systems search for explosives in indirect ways, such as detecting gamma rays emitted from neutron interactions. A system is needed which can probe directly for explosives through first order interactions. The most accurate method would be to identify the number densities of the elements which make up explosives. Using a fast neutron probe in a neutron transmission/attenuation system would be ideal, because the neutrons can penetrate the sample and interact directly with the atoms. Neutron detectors would form a critical component of such a system.

It is well known that, in general, neutron detectors respond to gamma rays as well as neutrons. This is especially true for neutron detectors that are used in fast neutron time of flight experiments. These gamma rays can be considered as background events and the elimination of these background counts would decrease the uncertainty of the parameter being measured. Hence, it is important to develop techniques to discriminate the background gamma rays from the neutron counts.

In many neutron measurements one wishes to count neutrons coming from a given neutron source, but there may be neutrons coming from other neutron sources or scattered neutrons from the given source which would, if counted, contribute to the background. One source of backgrounds is neutrons which scatter from one detector to adjoining detectors in a neutron detector array. Hence, again it is important to develop techniques to discriminate against neutrons coming from neutron sources other than from the given neutron source.

Neutron-gamma ray discrimination has been accomplished in the past by the use of pulse shape discrimination. See, for example, *"RADIATION DETECTION AND MEASUREMENT"* by Glenn F. Knoll, Chapter 17, John Wiley & Sons, New York (1989). This technique makes use of the fact that certain neutron detectors, such as stilbene and certain liquid scintillators, have a different decay time for neutrons than for gamma rays. Various electronic circuits have been developed that use the different decay times of the neutron and gamma rays to discriminate between the two. This technique works quite well so long as the count rate is not too high. However, even with modem electronics, the count rate for good resolution is limited to about 50,000 counts per second. In many measurements, the count rate needs to be up to about 500,000 to 1,000,000 counts per second. For this reason, there is a need for new and different techniques for discriminating between neutrons and gamma rays at high count rates.

A fiber optics neutron detector was proposed by Thomas G. Miller, Welman Gebhart, Lee Hilbert and George Edlin (see *"Fiber Optics Neutron Detectors"*, presented at the Workshop on Scintillating Fiber Detector Development for the SSC, Nov. 14–16, 1988). A fiber optics bundle is aimed at a neutron source so that the neutrons are incident on the ends of the fiber optics bundle, along the axis of the bundle. The opposite end of the fiber optics bundle is incident on an intensifier, which in turn is positioned against a neutron detector. The optical fibers have square cross section and measure 300 microns by 300 microns. The number of fibers traversed is an indication of the directionality of an incoming neutron. A specialized detector such as a charged coupled device (CCD) is required for this neutron detector. Such detectors do not have a fast time response and cannot be used where neutron energy is measured using time-of-flight techniques.

U.S. Pat. No. 5,155,366 describes a fiber optics neutron detector. A fiber optics bundle has a PM tube attached to each end. The fiber optics bundle is made up of an array of square fiber optics light pipes that form a checkerboard pattern. At one end of the bundle every other fiber is non-transmissive of light, forming a checkerboard pattern. At the other end of the bundle, the ends of the other fibers are blacked out. Hence, for an event that occurs in only one fiber, only one of the PM tubes will receive a signal. For events that occur in two or more of the fibers, signals will be received from each of the PM tubes almost simultaneously. If the bundle is aimed toward a neutron source, neutrons from the source will predominately stay in one fiber while neutrons coming from other directions will tend to cross two or more fibers. Gamma rays are detected by Compton scattering from electrons in the detector. Electrons are light and have a relatively long mean free path recoil electrons and will tend to cross two or more fibers. Hence, a coincidence pulse will tend to indicate a background pulse and an anti-coincidence pulse will tend to indicate a true event and will be so recorded.

The fiber optics neutron detector by Miller above must be aimed at the neutron source (along the fiber axis) and hence neutrons must pass through one of the PM tubes (and perhaps some electronics such as a voltage divider). This lowers the efficiency of the detector.

A directional scintillation counter for 14 MeV neutrons is described by Stelson and Berko (*A Directional Neutron Counter for Neutrons* by R. F. Stetson and S. Berko, Nuc. Instr. & Meth. 6 (1960) 94–95). In this counter, one and two mm sheets of scintillator material are used as the scintillator material. The sheets are placed sufficiently far apart so that recoil protons from one sheet cannot reach another sheet. To further assure that recoil protons from one sheet cannot reach another sheet, the space in between is filled with a material which tends to absorb any recoil protons leaving a sheet. The detector measures directionality of 14 MeV neutrons by measuring the counting ratio of neutrons entering along the axis to those entering perpendicular to the axis. The ratio is as high as 1000 for a bias setting of 90% of the maximum pulse height. This detector disadvantageously operates only at reaction energies of 14 MeV or higher. Also, the detector does not discriminate gamma rays from neutrons.

Another directional neutron counter is described by Thompson (*Directional Scintillation Counter* by M. A. Thompson, Rev. Scien. Instr. 29 (1958) 1149) for 14 MeV and 2.8 MeV neutrons. Thompson uses 0.10 mm diameter capillary tubes filled with xylene, terphenyl and POPOP. The capillary tubes are mounted in a pyrex test tube and PM tubes are mounted at both ends. The space between the tubes is filled with water. Defining directionality, R, as (axial counting rate)/(broadside counting rate), and efficiency, E, as number of neutrons counted/number of neutrons entering counter in axial position, Thompson measured R=60 and efficiency E=0.1% for 2.8 MeV neutrons. This detector also does not discriminate gamma rays from neutrons. Also, the relatively low efficiency of this detector in terms of count rate, and measuring directionality, would not permit this detector to be used in a contraband detection system, which requires high efficiency in these areas.

A neutron scintillation counter is needed that has directionality and at the same time can discriminate neutrons from gamma rays at count rates of at least 500,000 counts per second. Such a neutron counter should also be able to discriminate background neutrons and background gamma rays simultaneously.

In view of the foregoing concerns regarding the prior art, it is the object of the present invention to provide a neutron scintillating detector that has a more efficient capability in terms of measuring directionality and count rate than existing neutron detectors and also has the ability to discriminate neutrons from gamma rays at count rates of at least 500,000 counts per second.

SUMMARY OF INVENTION

A neutron detector is constructed of optical fibers comprised of at least two different types of plastic scintillator and arranged in alternating slabs or in fibers with a square cross-section arranged in a checkerboard pattern. One type of scintillator emits photons in the lower portion of the electromagnetic spectrum (typically from about 400 nanometers to about 500 nanometers) and the other type of scintillator emits photons in the upper portion of the electromagnetic spectrum (typically from about 500 nanometers to about 700 nanometers). An example of a plastic scintillator which emits photons only in the higher portion of the electromagnetic spectrum is Bicron BCF28. An example of a plastic scintillator which emits photons only in the lower portion of the electromagnetic spectrum is Bicron BC-418. The optical fibers alternate between the two different types of optical fibers, so that an optical fiber which emits only photons in the upper spectrum is contiguous only to optical fibers which emit photons only in the lower end of the spectrum and optical fibers which emit photons only in the lower end of the spectrum are contiguous only to optical fibers which emit photons only in the upper end of the spectrum. A clading is applied to the fibers to convert them into light pipes and to prevent the lower wavelength fibers from exciting the higher wavelength fibers. Two PM tubes view one end of the scintillator so that each PM tube can view the ends of all optical fibers. A low-band pass filter is placed in front of one of the PM tubes so that the tube can see signals from the fiber that emits only in the lower portion of the electromagnetic spectrum. A high band pass filter is placed in front of the other PM tube so that it can only see photons emitted by a fiber which emits photons only in the upper portion of the electromagnetic spectrum. When the detector is pointed toward the neutron source (fiber axis toward the neutron source) the detected neutrons which proceed from the source will tend to stay in one optical fiber, hence a signal from only one of the PM tubes produces an anti-coincident signal. Background neutrons and/or gamma rays will tend to cross contiguous optical fibers and hence signals will come from both PM tubes, producing coincident signals. Since the decay time of plastic scintillators are a few nanoseconds, count rates should approach a million counts per second. Although the neutron detector and filter means are described as having two types of optical fibers and filters (corresponding to the higher and lower positions of the electromagnetic spectrum), multiple types of optical fibers and filters (corresponding to different portions of the electromagnetic spectrum) could be used.

BRIEF DESCRIPTION OF THE DRAWINGS

The foregoing and other objects, features, and advantages of the invention will be apparent from the following more particular description of preferred embodiments as illustrated in the accompanying drawings in which references characters refer to the same parts throughout the various views. The drawings are not necessarily to scale, emphasis instead being placed upon the principles of the invention.

DETAILED DESCRIPTION OF THE DRAWINGS

Figure 1:
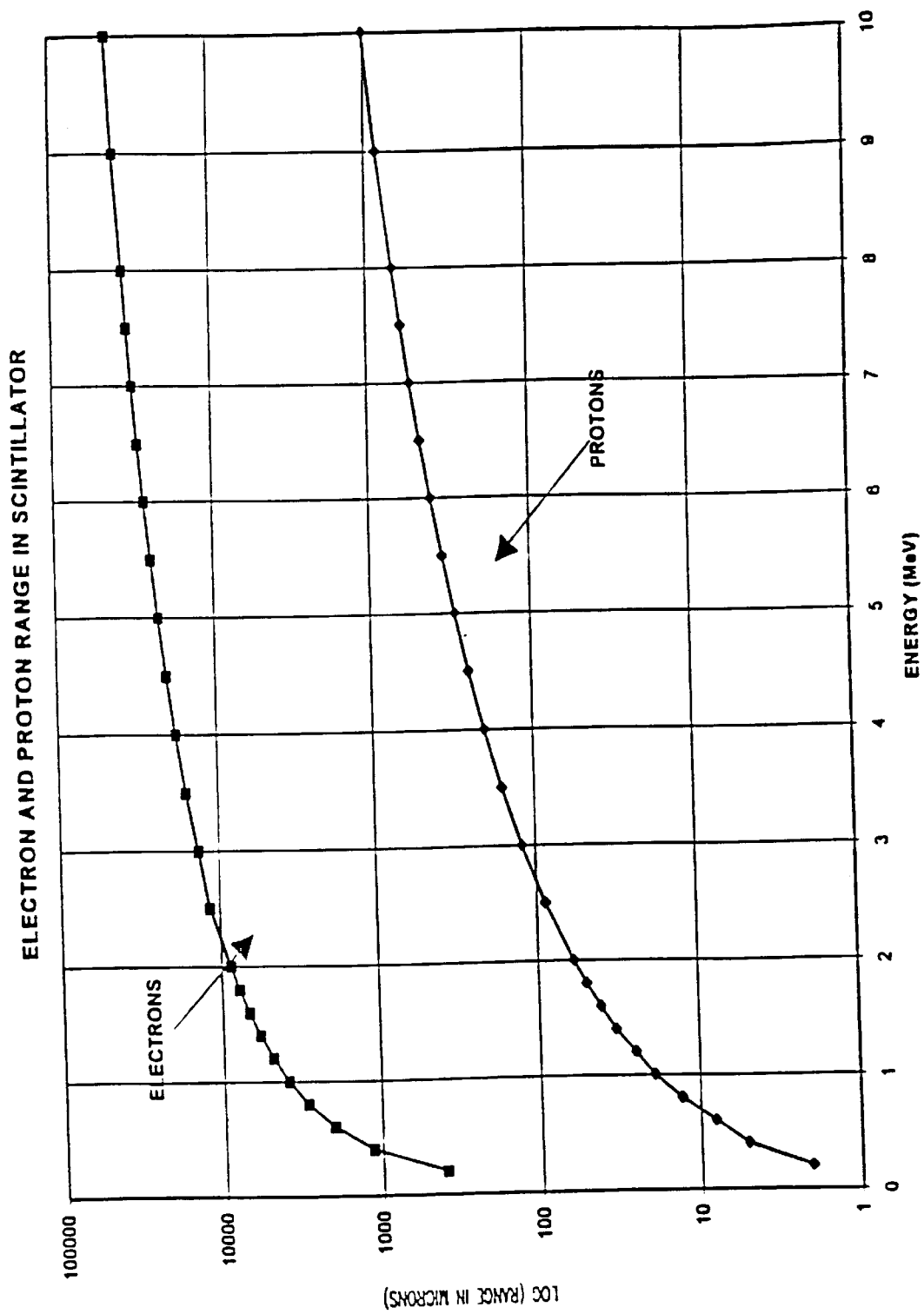
FIG. 1 is a graphical view showing electron and proton ranges in microns in the scintillator as a function of energy in MeV.

FIG. 1 shows a graph of the range of protons and electrons in plastic scintillator material. FIG. 1 shows that a 1 MeV recoil proton will travel about 11 microns before coming to rest. FIG. 1 shows that a 1 MeV Compton scattered electron will travel about 6000 microns in the scintillator before coming to rest.

Figure 2:
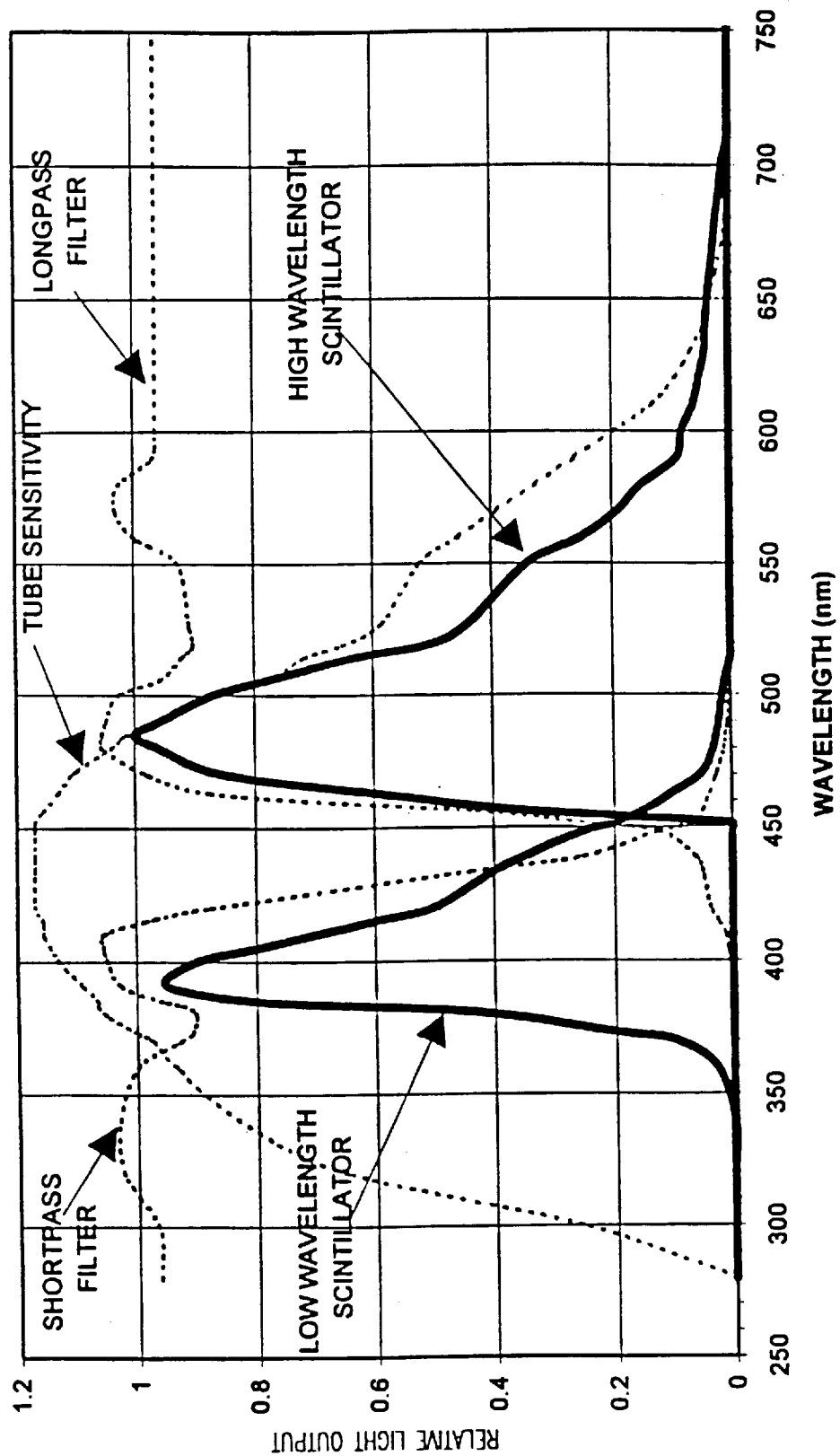
FIG. 2 is a graphical view showing the emitted spectra of the scintillators along with the sensitivity of the PM tube. Also shown in the view is the cut-off for the filter for the PM tube that emits the low wavelength photons and the cut-on for the filter on the PM tube that emits the long wavelength photons.

FIG. 2 shows the wavelength sensitivity of the PM tube along with the emission spectrum of two plastic scintillators. FIG. 2 also shows typical transmissivity curves for a cut-on filter and a cut-off filter.

Figure 3:
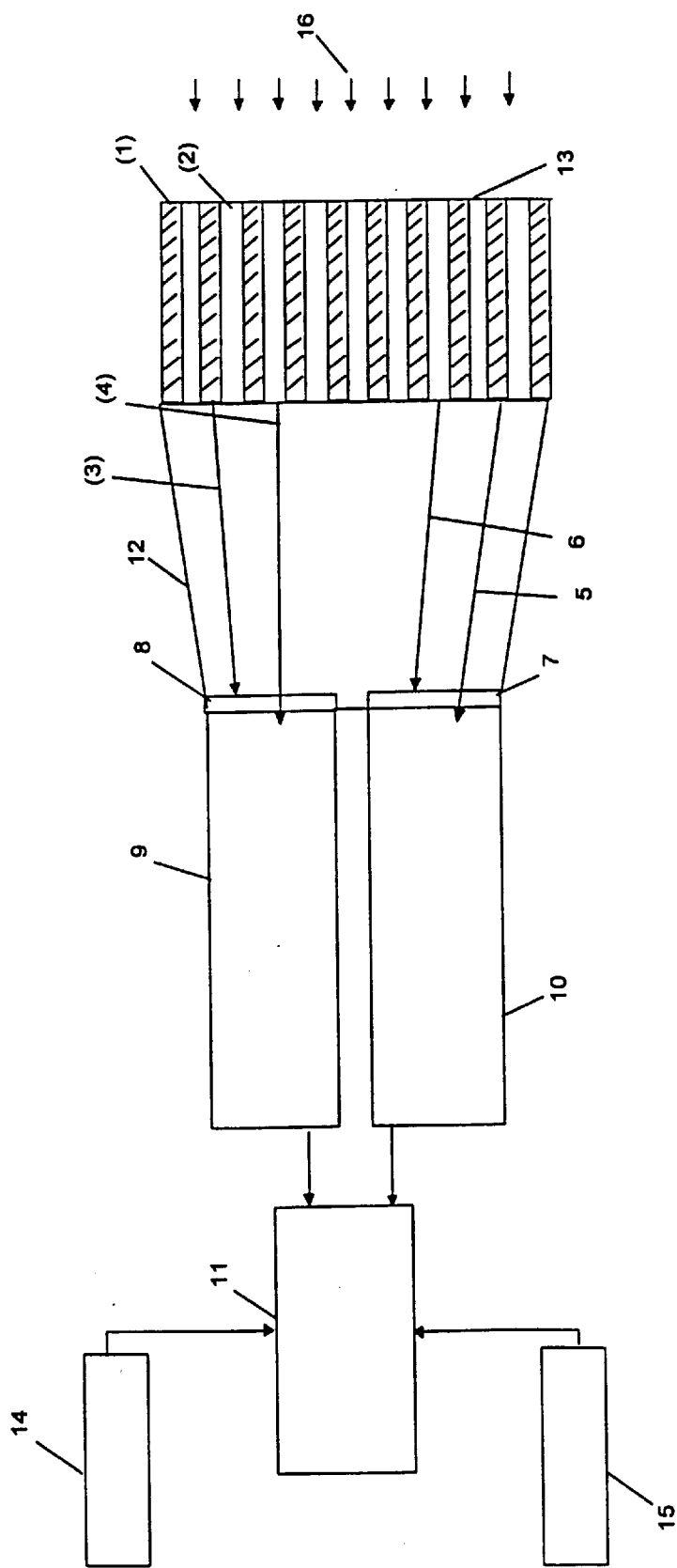
FIG. 3 is a partial schematic view of a neutron directionality/neutron-gamma discrimination apparatus.

FIG. 3 shows a neutron directionality/neutron-gamma discrimination apparatus. The apparatus includes a scintillator 13, a light pipe 12, a short pass filter 7 attached to a PM tube 10, a long pass filter 8, attached to a PM tube 9, a signal processing unit 11, a neutron counter 14, and a background counter 15.

The PM tubes 9, 10, are conventional PM tubes of the type that produce an electrical signal when a light pulse is incident. Typically, the PM tubes respond to light photons from about 300 nanometers to about 700 nanometers. One of the PM tubes 10 has a short pass filter 7 attached to it, which allows light photons from the lower portion of the spectrum, about 350 to 450 nanometers, to pass on to the PM tube. The other PM tube 9, has a long pass filter 8 attached which allows long wavelength photons, typically, 450–700 nanometer photons, to pass through to the PM tube. The PM tubes have their own voltage dividers attached. The scintillator 13 consists of optical fibers which are either slabs 1, 2 of scintillator material or of square optical fiber scintillator material (not shown). The slabs 1, 2 alternate in different scintillator material so that one emits only low wavelength photons 1 and the other 2 emits only high wavelength photons. Photons are emitted when the scintillator material is excited by neutrons or gamma rays. Photons emitted by the low wavelength scintillator 1 can enter the PM tube 10 through the low wavelength filter 7, but cannot enter PM tube 9 because they are blocked by long wavelength filter 8. Likewise, high wavelength photons can enter PM tube 9 through long wavelength filter 8, but cannot enter PM 10 because they are blocked by short wavelength filter 7. A light pipe 12 allows the photons to pass from the scintillator 13 to the PM tubes with only a small amount of attenuation.

When the neutron detector 13 is aimed toward the neutron source, the source neutrons enter the neutron detector parallel to the axis of the scintillator. These target neutrons tend to stay within a single slab 1,2 because the angular distribution is forward-peaked. The angular distribution is forward-peaked because low energy neutrons (below about 8 MeV) predominately scatter from hydrogen atoms in the neutron detector and they have a $\cos\phi$ distribution, where $\phi$ is the laboratory scattering angle. The energy of the scattered proton varies as $\cos^2\phi$. The range of the scatter varies approximately as $E^{3/2}$, hence the product of the range of the protons scattered at $\phi$ and the number scattered at $\phi$ varies as $\cos^4\phi$ resulting in a highly forward-peaked distribution. Hence a neutron from the neutron source tends to stay in fiber slab 1 if it enters slab 1, or slab 2 if it enters slab 2, and only one PM tube will receive a signal.

Background neutrons that enter at right angles (or some other angle) can more easily penetrate into an adjacent slab and hence a signal from both PM tubes signal a background event.

Gamma rays Compton scatter from electrons in the scintillator 13, creating electrons that have long ranges compared to the thickness of a single slab of the scintillator. Hence the probability is high that most gamma rays will cross two or more slabs, which will result in signals from both PM tubes which the signal processing unit 11 recognizes as a background event.

Figure 4:
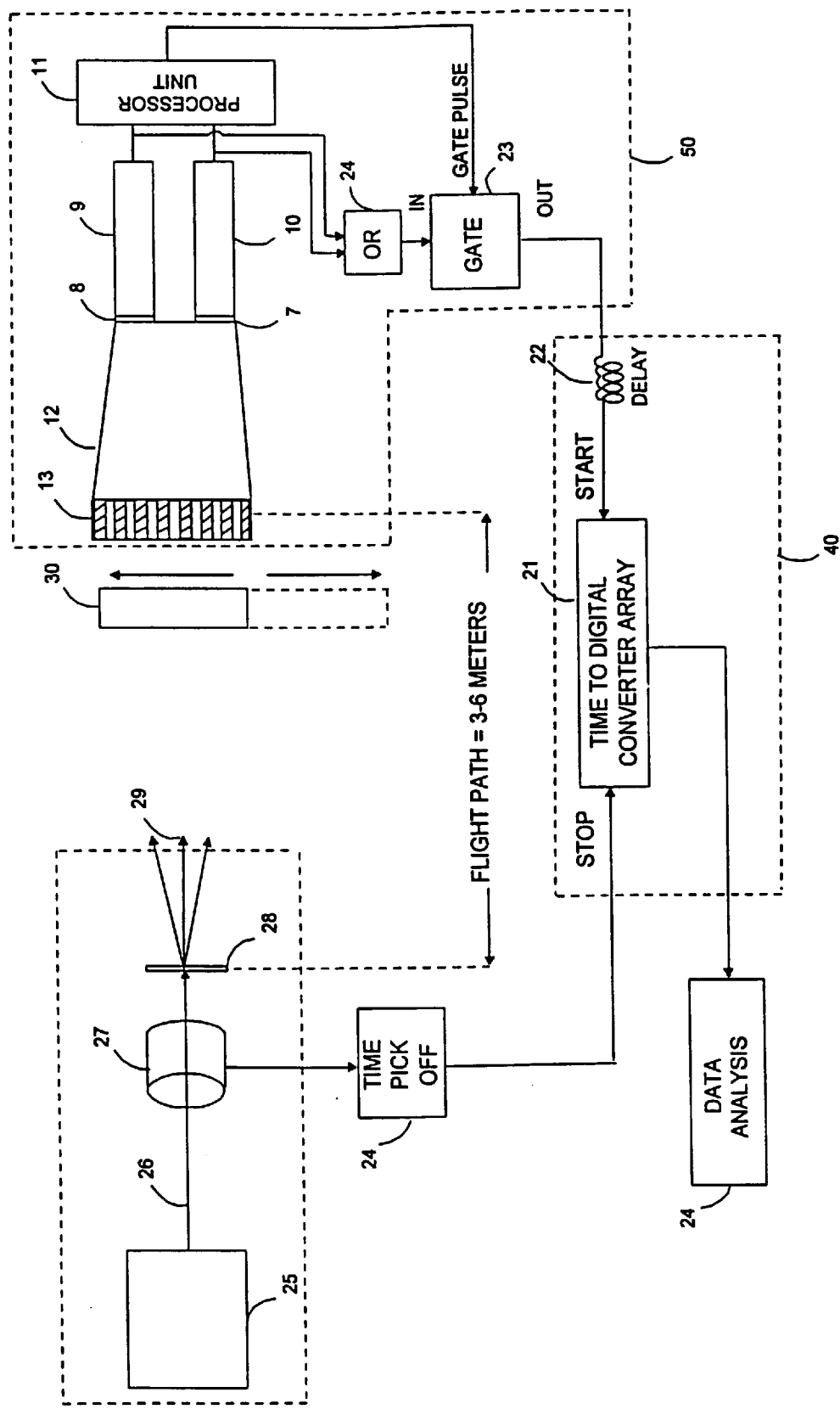
FIG. 4 shows a contraband detection system incorporating the neutron directionality/neutron-gamma discrimination apparatus for background reduction.

FIG. 4 shows an example of the use of the neutron directionality/neutron-gamma discrimination apparatus in a contraband detection system. The system is being utilized in the contraband detection system to reduce background neutrons and simultaneously to reduce background gamma rays. The contraband detection system detects contraband in sealed containers using Fast Neutron Transmission Spectroscopy (FNTS).

In FIG. 4, a neutron source assembly 60 produces a pulsed neutron beam by allowing a pulsed deuteron beam 26, produced by a pulsed deuteron source 25, to impinge on a thick beryllium target 28. The pulsed deuteron beam 26 produces a pulse each time a pulse of deuterons pass through a beam pick-off 27. The pulse from the beam pick-off 27 is detected, amplified and standardized by the time pick-off 24. The time pick-off supplies the stop signal to the Time to Digital Converter (TDC). A pulsed 'white' neutron beam 29 is produced when the pulsed deuteron beam 26 impinges on the thick beryllium target 28. A 'white' neutron beam means that neutrons are produced over a wide energy range depending of the energy of the deuteron beam. For the quoted reference, a 5 MeV neutron beam was used, resulting in neutron energies from about 5 MeV to about 8 MeV.

A neutron detector assembly 50 contains the neutron scintillator 13 and a light pipe 12 to transmit the photons to the PM tubes 9, 10 through band pass filters 7, 8. Signals from either PM tube can pass through an or circuit, but can only pass through the gate 23 provided it is a valid pulse as determined by the processor unit 11. A sealed container (suitcase) 30 can be moved in and out from the front of the neutron scintillator 13. When pulses from the PM tubes are valid, the pulse is passed from the neutron detector assembly to the TDC of the neutron spectroscopy assembly. Assume the case of a neutron (29) from the neutron source impinging on the neutron detector 13. It is highly probable that the recoil proton from this neutron will stay within one slab, either 1 or 2, and hence only one of the PM tubes will provide a signal. The processor 11 will recognize this as a valid event and will transmit a gate pulse to gate 23, which in turn will allow the pulse from the or circuit 24, to transmit that particular pulse to the TDC. Now consider a neutron impinging on the detector broadside, or perpendicular to the axis of the detector. It is now highly probably that the recoil proton from this neutron will cross at least two slabs 1, 2 of the detector assembly 13. The processor unit 11, will now receive pulses from both PM tubes and will recognize this event as a background event and will not transmit a gate pulse to the gate 23. Hence the background pulse has been blocked.

Consider a background gamma ray causing scintillations in the neutron detector 13. For gamma ray energies of interest, the principal interaction in the neutron detector will be Compton scattering of the interacting gamma ray. This interaction produces an electron in the neutron detector 13. From FIG. 1, it can be seen that the range of electrons of about 0.3 MeV and up is more than 1000 microns. Hence the probability is high that these electrons will cross two or more slabs of the detector. This will result in pulses from both PM tubes, which the processor unit 11 will recognize as a background event. The processor 11 will not pass a gate pulse to the gate 23, hence the background pulse from the or circuit 24 is blocked. The neutron spectroscopy assembly 40 produces a time-of-flight spectrum of the neutrons interacting with the detector by measuring the time it takes a neutron to travel from the target to the neutron detector. This time-off-light spectrum can then be converted to an energy spectrum if required. The time-of-flight of each detected neutron is measured by the neutron spectroscopy assembly 40 by allowing a valid event from the gate 23 to start a TDC 21. The stop pulse for this start pulse is from the time pick-off 24 from the neutron source assembly. A delay is inserted in the start pulse to assure that the stop pulse comes after the start pulse. It is common practice in neutron spectroscopy to put the low count rate source on the start rather than the stop to keep the TDC less busy. For each sample, a neutron spectrum is determined with the sample in and then with the sample out. These results are then passed to the data analysis assembly 24. The data analysis assembly 24 determines the neutron attenuation versus neutron energy defined as Ln(No/N) on a channel by channel basis, where No represents the neutron spectrum without the sample and N represents the neutron spectrum with the spectrum. The neutron attenuation curve is characteristic of the sample and is different for each sample. Hence, the neutron attenuation spectrum for a suitcase with contraband is different from a suitcase without contraband.

The embodiments of the invention in which an exclusive property or privilege is claimed are defined as follows:

1. Apparatus for detecting a particular type of particle, the apparatus comprising:

first photomultiplier means for producing a first signal when a light pulse is incident on the first photomultiplier means;

first filtering means for allowing only light pulses in a specified portion of the electromagnetic spectrum to be incident on the said first photomultiplier means;

at least one additional photomultiplier means for producing an additional signal when a light pulse is incident on said additional photomultiplier means;

at least one additional filtering means for allowing only light pulses in a different specified portion of the electromagnetic spectrum to be incident on said additional photomultiplier means;

scintillator means for generating light photons upon the incidence thereon of ionizing radiation, the scintillator means comprising a plurality of optical fibers of different types, each type of which emits photons in one of said specified portions of the electromagnetic spectrum corresponding to one of said filtering means, said optical fibers being arranged substantially contiguously along at least a first direction essentially perpendicular to a length dimension of the optical fibers, with contiguous optical fibers along the first direction being of different types; and signal processing means for processing the first signal from the first photomultiplier means and the additional signal from the additional photomultiplier means to provide an indication of when a particular type of particle in the energy range of interest is detected by said scintillator means.

2. The apparatus of claim 1, wherein said energy range of interest is on the order of from about 0.5 MeV to about 8.0 MeV, and wherein the maximum dimension of the optical fibers in said first direction is on the order of about 100–250 microns.

3. The apparatus of claim 1, further comprising gating means responsive to the signal processing means for gating therethrough signals from the photomultiplier means.

4. The apparatus of claim 3, further comprising:

means for creating particles of the type to be detected by the scintillator means;

means connected to particle creating means and to the gating means for determining a time of flight of a particle between the particle creating means and the scintillator means; and means connected to the time of flight determining means for providing an energy spectrum indicative of a substance situated in a path between the particle creating means and the scintillator means.

5. The apparatus of claim 1, wherein the ends of said optical fibers are located proximate to each of the photomultiplier means are arranged in an essentially checkerboard pattern.

6. The apparatus of claim 1, wherein said optical fibers are arranged in an essentially alternating pattern and common ends of which are proximate to each of the photomultiplier means.

7. A method for detecting a particle in an energy range of interest and for discriminating between the particle and background radiation, the method comprising the steps of:

connecting a scintillating medium to a plurality of photomultipliers, the scintillating medium being in the form of a plurality of types of optical fibers which transmit light pulses in different portions of the electromagnetic spectrum, which are arranged substantially contiguously along at least a first direction, the first direction being essentially perpendicular to a length dimension of the optical fibers, and which are arranged in an alternating pattern, in which contiguous optical fibers are of different types;

optically coupling a filtering means to each of said photomultipliers, each of which filtering means allows only light photons from a different one of said portions of the electromagnetic spectrum to be incident on the respective photomultiplier;

using the photomultipliers to detect photons caused by ionization in the scintillating medium and to provide output signals upon the detection of photons;

processing said photomultiplier output signals to determine whether a detected photon is indicative of a particle in the energy range of interest.

8. A method for detecting a particle in an energy range of interest and for discriminating between the particle and background radiation, the method comprising the steps of:

providing a scintillating medium between two photomultipliers, the scintillating medium being in the form of a plurality of optical fibers, the optical fibers being arranged substantially contiguously along at least a first direction, the first direction being essentially perpendicular to a length dimension of the optical fibers, each of the optical fibers having a first end and an opposing second end, each of which said optical fibers emit light pulses only in a higher portion of the electromagnetic spectrum or only in a lower portion of the electromagnetic spectrum, with contiguous ones of the optical fibers emitting light pulses only in the higher portion of the electromagnetic spectrum alternating with optical fibers which emit photons only in the lower portion of the electromagnetic spectrum;

connecting a filtering means to a first photomultiplier tube which allows only light pulses in the lower portion of the electromagnetic spectrum to be incident on the said first photomultiplier;

connecting a filtering means to a second photomultiplier tube which allows only light pulses in the higher portion of the electromagnetic spectrum to be incident on the said second photomultiplier;

producing output signals from the first and second photomultipliers when photons are incident thereon;

processing said photomultiplier output signals to determine whether a detected photon is indicative of a particle in the energy range of interest.

9. The method of claim 8, wherein the determination of whether a photon is indicative of a particle in the energy range of interest is based on the sequence and timing of output signals from the first and second photomultipliers.

10. The method of claim 8, in which the optical fibers which emit light pulses only in the higher portion of the electromagnetic spectrum are comprised of Bicron BCF 28.

11. The method of claim 8, in which the optical fibers which emit light pulses only in the lower portion of the electromagnetic spectrum are comprised of Bicron BD-418.

12. A directional neutron-gamma ray discrimination detector, comprising:
(a) one or more plastic scintillator fibers of a first type which emits light photons having wavelengths within a first region of the electromagnetic spectrum in response to the incidence thereon of neutrons and/or gamma rays;
(b) one or more plastic scintillator fibers of a second type which emits light photons having wavelengths within a second region of the electromagnetic spectrum in response to the incidence thereon of neutrons and/or gamma rays;
(c) each of said first-type fibers and second-type fibers having a first end and an opposing second end and a lengthwise dimension extending therebetween;
(d) said first-type fibers and said second-type fibers being substantially contiguous to one another in a direction substantially perpendicular to said lengthwise dimension thereof, with said first-type fibers alternating with said second-type fibers such that first-type fibers are contiguous only with second-type fibers and second-type fibers are contiguous only with first-type fibers;
(e) first and second photomultipliers optically coupled to the same end of all of said first-type fibers and said second-type fibers for selectively producing signals in response to light photons emitted by said first-type fibers and said second-type fibers, respectively; and
(f) means for processing the signals from said first and second photomultipliers to identity signals resulting from neutrons incident on the other end of said fibers in directions generally parallel to the lengthwise direction of said fibers and to discriminate against signals resulting from neutrons incident on said fibers in other directions or from gamma rays.

13. The detector of claim 12, wherein said signal processing means processes signals produced substantially simultaneously by both said first and second photomultipliers as coincident signals, indicative of background neutrons and/or gamma rays, and processes signals produced by only one of said first and second photomultipliers as anti-coincident signals, indicative of neutrons incident on said other end of said fibers in directions generally parallel to the lengthwise direction thereof.

14. The detector of claim 12, wherein:
said first-type fiber emits light photons having wavelengths within the range of about 300–450 nanometers; and
said second-type fiber emits light photons having wavelengths within the range of about 450–700 nanometers.

15. The detector of claim 12, wherein each of said first-type fibers and said second-type fibers is clad to form a light pipe.

16. The detector of claim 12, wherein:
each of said first-type fibers and said second-type fibers is substantially rectangular in cross section; and the rectangularly-shaped first-type and second-type fibers are alternated in the direction perpendicular to the lengthwise dimension of said fibers.

17. The detector of claim 16, wherein the dimension of each fiber in said substantially perpendicular direction is within the range of about 100–250 microns.

18. The detector of claim 17, wherein both the lengthwise dimension and the width of each rectangularly-shaped fiber are within the range of about 2–4 centimeters.

19. The detector of claim 12, wherein each of said first-type fibers and said second-type fibers is substantially square in cross section.

20. The detector of claim 19, wherein the cross sectional dimensions of each said first-type and second-type fibers are within the range of about 100–250 microns by about 100–250 microns.

21. The detector of claim 20, wherein the length of each said first-type and second-type fiber is within the range of about 2–4 centimeters.

22. The detector of claim 20, wherein a plurality of said first-type fibers and a plurality of said second-type fibers are alternately arranged in a substantially checkerboard pattern as viewed in cross section.

23. A directional neutron detector, comprising:
(a) one or more plastic scintillator fibers of a first type which emits light photons having wavelengths within a first region of the electromagnetic spectrum in response to the incidence thereon of neutrons and/or gamma rays;
(b) one or more plastic scintillator fibers of a second type which emits light photons having wavelengths within a second region of the electromagnetic spectrum in response to the incidence thereon of neutrons and/or gamma rays;
(c) each of said first-type fibers and second-type fibers having a first end and an opposing second end and a lengthwise dimension extending therebetween;
(d) said first-type fibers and said second-type fibers being substantially contiguous to one another in a direction substantially perpendicular to said lengthwise dimension thereof, with said first-type fibers alternating with said second-type fibers such that first-type fibers are contiguous only with second-type fibers and second-type fibers are contiguous only with first-type fibers;

(e) each of said first-type fibers and said second-type fibers being sensitive to neutrons within the range of from about 0.5 MeV–8 MeV; and (f) each of said fibers having a dimension in said substantially perpendicular direction that is small relative to the range therein of Compton scattering electrons resulting from interactions with said fibers of gamma rays having energies within said energy range of sensitivity.

24. The detector of claim 23, wherein:

said first-type fiber emits light photons having wavelengths within the range of about 300–450 nanometers; and said second-type fiber emits light photons having wavelengths within the range of about 450–700 nanometers.

25. The detector of claim 23, wherein:

each of said first-type fibers and said second-type fibers is substantially rectangular in cross section; and the rectangularly-shaped first-type and second-type fibers are alternated in the direction perpendicular to the lengthwise dimension of said fibers.

26. The detector of claim 25, wherein the dimension of each fiber in said substantially perpendicular direction is within the range of about 100–250 microns.

27. The detector of claim 26, wherein both the lengthwise dimension and the width of each rectangularly-shaped fiber are within the range of about 2–4 centimeters.

28. The detector of claim 23, wherein each of said first-type fibers and said second-type fibers is substantially square in cross section.

29. The detector of claim 28, wherein the cross sectional dimensions of each said first-type and second-type fibers are within the range of about 100–250 microns by about 100–250 microns.

30. The detector of claim 29, wherein the length of each said first-type and second-type fiber is within the range of about 2–4 centimeters.

31. The detector of claim 29, wherein a plurality of said first-type fibers and a plurality of said second-type fibers are alternately arranged in a substantially checkerboard pattern as viewed in cross section.

32. The detector of claim 23, wherein said first-type fiber is comprised of Bicron BCF 28.

33. The detector of claim 23, wherein said second-type fiber is comprised of Bicron BD-418.

* * * * *

UNITED STATES PATENT AND TRADEMARK OFFICE
CERTIFICATE OF CORRECTION

PATENT NO. : 5,880,469

DATED : March 9, 1999

INVENTOR(S) : Dr. Thomas G. Miller

It is certified that error appears in the above-identified patent and that said Letters Patent is hereby corrected as shown below:

Col. 3, line 24, "electrons" should be deleted;
Col. 5, line 49, after "dividers attached." delete --The scintillator 13--;
Col. 5, line 50, before "consists" insert --The scintillator 13--;
Col. 6, line 39, "pass" should read --passes--;
Col. 6, line 46, "of" should read --on--;
Col. 7, line 30, "pick-off" should read --of pick-off--;
Col. 8, line 33, delete "are";
Col. 8, line 61, "photons;" should read --photons; and--
Col. 9, line 8, "emit" should read --emits--;
Col. 9, line 24, "thereon;" should read --thereon; and--;
Col. 9, line 41, "emits" should read --emit--;
Col. 9, line 46, "emits" should read --emit--;
Col. 10, line 26, "and the" should read --and--;
Col. 10, line 27, before "rectangularly-shaped" insert --the--;
Col. 10, line 39, "cross sectional" should read --cross-sectional--;
Col. 10, line 52, "emits" should read --emit--;
Col. 10, line 57, "emits" should read --emit--;
Col. 12, line 10, "cross sectional" should read --cross-sectional--.

Signed and Sealed this

Twenty-ninth Day of August, 2000

Attest:

Q. TODD DICKINSON

Attesting Officer

Director of Patents and Trademarks